United States Patent [19]
Heilbrunn

[11] Patent Number: 5,921,776
[45] Date of Patent: Jul. 13, 1999

[54] DISPOSABLE PROTECTIVE BARRIERS FOR USE WITH DENTAL INSTRUMENTS

[76] Inventor: Karl E. Heilbrunn, 305 E. 86th St., Apt. 6P, New York, N.Y. 10028

[21] Appl. No.: 09/034,974

[22] Filed: Mar. 5, 1998

Related U.S. Application Data

[60] Provisional application No. 60/040,038, Mar. 5, 1997.

[51] Int. Cl.[6] ........................................... A61L 1/16
[52] U.S. Cl. ............................................... 433/116
[58] Field of Search ............................................... 433/116

[56] References Cited

U.S. PATENT DOCUMENTS

| | | | |
|---|---|---|---|
| 1,162,941 | 12/1915 | Martin et al. | 433/116 |
| 2,073,137 | 3/1937 | Bimrose | 433/116 |
| 4,266,935 | 5/1981 | Hoppe | 433/116 |
| 4,723,912 | 2/1988 | Nieusma | 433/116 |
| 4,795,343 | 1/1989 | Choisser | 433/116 |
| 4,810,194 | 3/1989 | Snedden | 433/116 |
| 4,907,968 | 3/1990 | Eisner et al. | 433/116 |
| 5,197,875 | 3/1993 | Nerli | 433/116 |
| 5,228,851 | 7/1993 | Burton | 433/116 |
| 5,302,124 | 4/1994 | Lansing et al. | 433/116 |
| 5,328,368 | 7/1994 | Lansing et al. | 433/116 |

*Primary Examiner*—John J. Wilson
*Assistant Examiner*—Patrick A. Hilsmier
*Attorney, Agent, or Firm*—Arnall Golden & Gregory, LLP

[57] ABSTRACT

An inexpensive, time-efficient, and effective protective barrier device which provides protection against the transfer of contaminants such as infectious agents from one dental patient to another dental patient is provided. In particular, a barrier device is provided for attachment to a dental instrument. Dental instruments which can be directly protected include saliva ejector instruments and air/water supply instruments. Because the hands of the dental care provider or other user are protected from exposure to contaminating infectious agents, all dental instruments and accessories are indirectly protected. The barrier device includes a disposable sheath which can be positioned to shroud the instrument without encumbering its functionality. The device further includes a disposable probe which is integrally formed with the sheath and which is attached to the instrument along with the sheath.

6 Claims, 3 Drawing Sheets

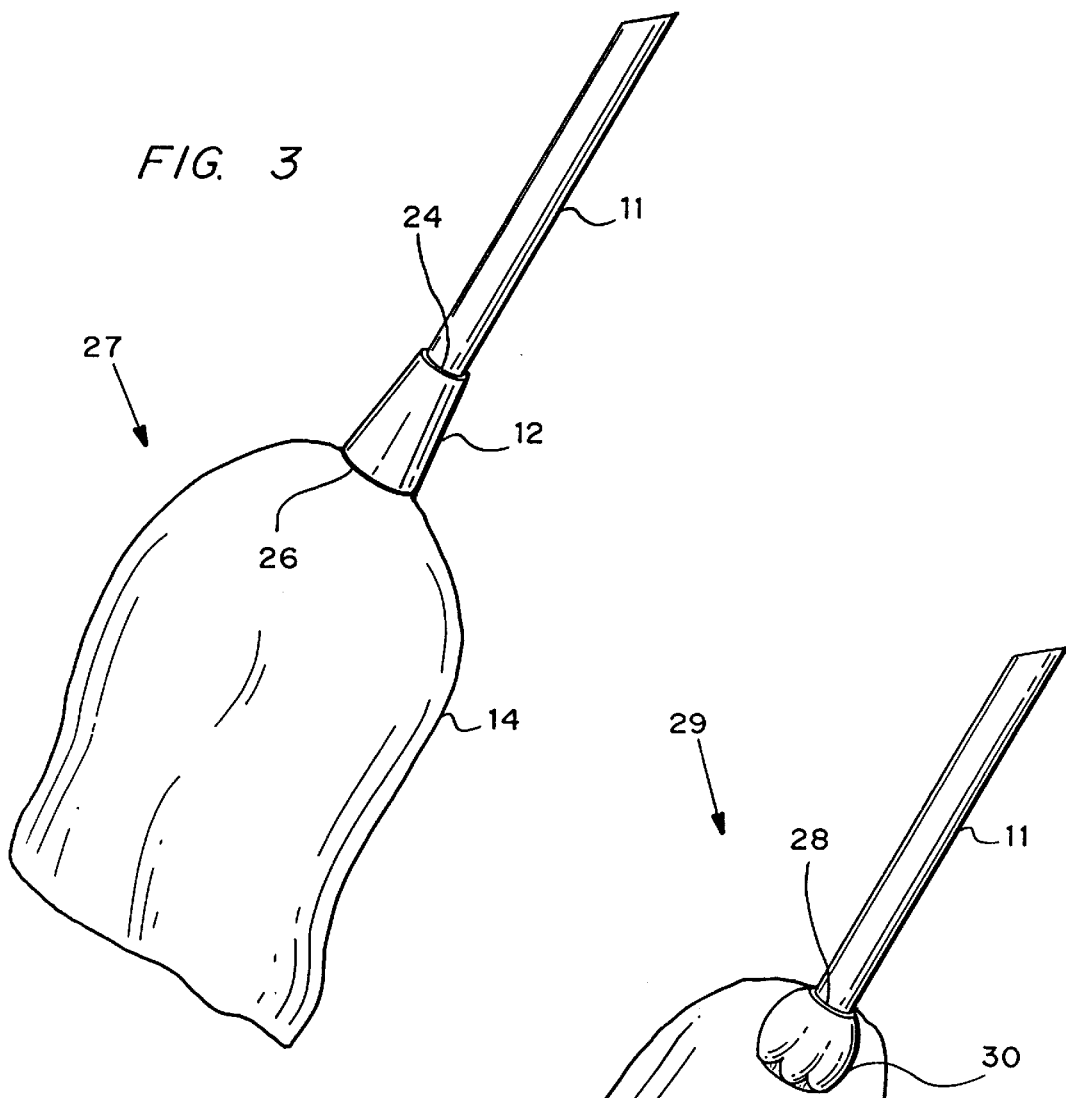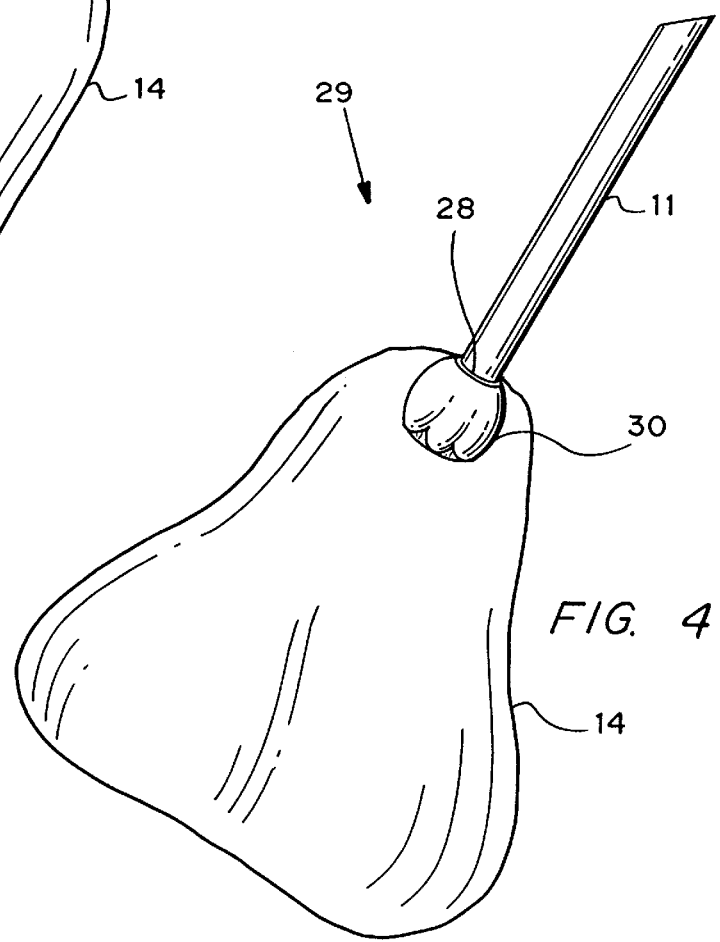

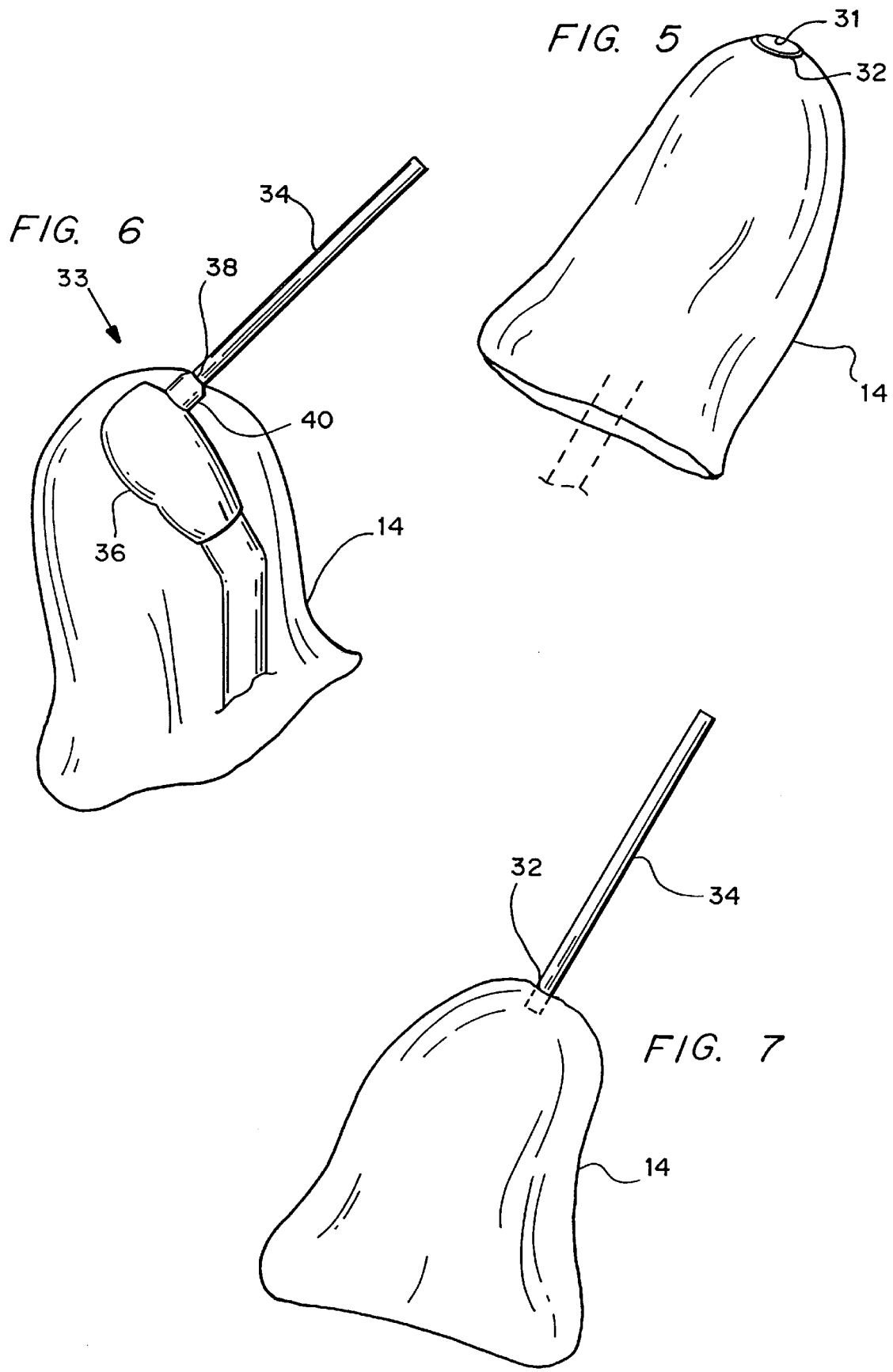

DISPOSABLE PROTECTIVE BARRIERS FOR USE WITH DENTAL INSTRUMENTS

This application claims the benefit of Provisional Application Ser. No. 60/040,038, filed Mar. 5, 1997.

FIELD OF THE INVENTION

This invention relates to protective barriers, and more particularly, to disposable protective barriers for use with dental instruments.

BACKGROUND OF THE INVENTION

Protection against infectious agents is important in the dental industry. Dental care providers strive to protect themselves and their patients from possible contamination. To help provide protection against contamination, dental care providers use disposable gloves which they typically change, at a minimum, after use with each patient. However, gloves can fail as a protective device because the instrument used by the wearer is not protected from contamination. In other words, after an infectious agent from one patient contaminates an instrument, the dental care provider can contact the agent on the instrument and then spread the agent to the next patient. Therefore, unless the instrument is replaced or sterilized between each patient, the dental care provider can spread the contamination on the instrument to subsequent patients. Replacing the instrument parts which are vulnerable to contamination is prohibitively expensive. Sterilizing the parts by autoclaving is time consuming. Sterilizing the parts by spraying with disinfectant is inadequate to effectively remove all contaminants.

The prior art discloses protective plastic sheaths for covering hand held dental tools. For example, U.S. Pat. No. 4,810,194, issued to Snedden, discloses a plastic sheath for protecting an evacuator or suction device. The plastic sheath is attached to an adaptor which connects a disposable evacuator tube to the valve body. This device requires assembly before use, first to attach the adaptor to the valve and then to attach the disposable evacuator tube to the adaptor. Such assembly takes time and also introduces risk of contamination, in that there is handling of the evacuator tube during assembly and also there is the risk that the evacuator tube will be reused. Other prior art patents also disclose sheaths for use in protecting dental tools wherein at least a portion of the tool is covered with a plastic sleeve. See, for example, U.S. Pat. No. 2,073,137, issued to Bimrose, U.S. Pat. No. 4,266,935, issued to Hoppe, and U.S. Pat. No. 4,907,968, issued to Eisner and Becker. None of these prior art patents teaches a disposable protective barrier that can be assembled on the device in one simple step and that is completely disposable.

Therefore, it is an object of the present invention to provide an inexpensive, time-efficient, and effective protective barrier for a dental instrument that will protect against the transfer of contaminants from one dental patient to another dental patient.

It is also an object of the present invention to provide an inexpensive, time-efficient, and effective method to protect against the transfer of contaminants from one dental patient to another dental patient via a dental instrument.

SUMMARY OF THE INVENTION

An inexpensive, time-efficient, and effective protective barrier device which provides protection against the transfer of contaminants such as infectious agents from one dental patient to another dental patient is provided. In particular, a barrier device is provided for attachment to a dental instrument. Dental instruments which can be directly protected include saliva ejector instruments and air/water supply instruments. Because the hands of the dental care provider or other user are protected from exposure to contaminating infectious agents, all dental instruments and accessories are indirectly protected.

The barrier device includes a disposable sheath which can be positioned to shroud the instrument without encumbering its functionality. The device further includes a disposable probe which is integrally formed with the sheath and which is attached to the instrument along with the sheath.

BRIEF DESCRIPTION OF THE DRAWINGS

FIG. 3 illustrates the barrier device of FIG. 1 wherein the probe, nipple and sheath are a single unit.

FIG. 4 illustrates a second embodiment of a barrier device wherein the probe and sheath are a single unit.

FIG. 5 illustrates a sheath manufactured as a unitary item.

FIG. 6 illustrates a barrier device installed on a water/air supply instrument, wherein the device includes a probe and a sheath.

FIG. 7 illustrates the device of FIG. 6 wherein the sheath and probe are an integral unit.

DETAILED DESCRIPTION OF THE INVENTION

The sheath used in the protective device is impervious to infectious agents and, preferably, impervious to fluids. Preferably, the sheath is formed of an inexpensive, fluid impervious plastic film. Alternatively, the sheath can be manufactured from a multilayered sheet where a first layer is absorbent and a second layer is fluid impervious.

In a preferred embodiment, the device is available as a disposable integral unit wherein the sheath is attached to extend circumferentially from a plastic or rubber nipple which is connected to a probe. In one embodiment, the sheath, nipple and saliva ejector probe are manufactured as a single disposable unit. Alternatively, the unit can be assembled before use. The unit connects to an instrument, such as a saliva ejector instrument or air/water supply instrument such that the sheath encircles around the proximal section of the instrument and the liquid waste or supply hose. The sheath extends over a length of the instrument such that a hand positioned upon the instrument will contact the sheath and will not contaminate, or become contaminated by, the instrument.

In an alternative embodiment, the sheath is manufactured as a single article, and the sheath includes an orifice or a region at which an orifice can be easily formed by the user. The sheath can be connected at the orifice to any instrument or dental accessory. Additionally, fasteners such as tape, elastic bands, or ties can be used to further secure the sheath as desired.

The method of protecting dental instruments and users of dental instruments generally includes providing a protective barrier, connecting the barrier to the instrument to be protected, and discarding the barrier after a patient has been treated.

Figure 1:
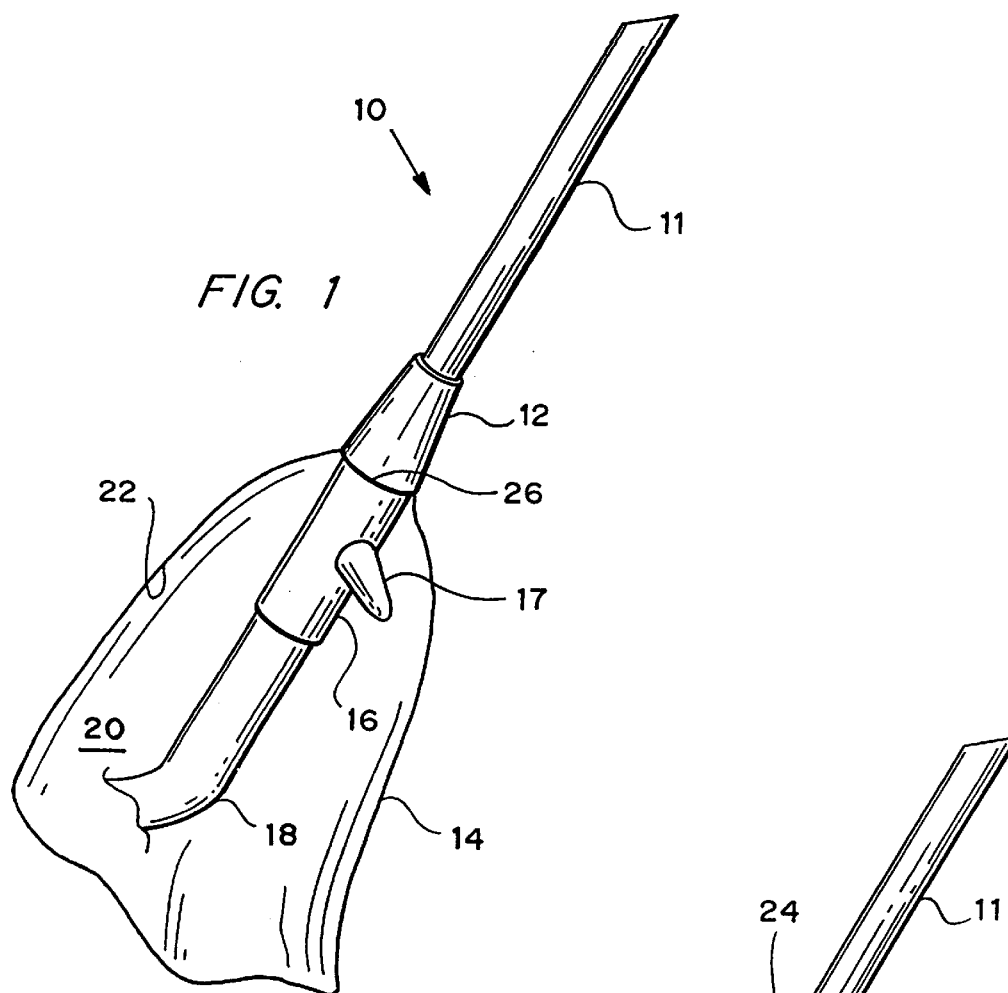
FIG. 1 illustrates a barrier device installed on a saliva ejector instrument, wherein the device includes a probe, a connecting nipple, and a sheath.

Particular embodiments of the device are illustrated in the Figures, in which like numerals indicate like parts throughout the several Figures. FIG. 1 illustrates a portion of a saliva ejector instrument 10, having a probe 11, nipple connector 12, sheath 14, valve 16, and waste disposal hose 18. Probe 11 is preferably formed of plastic and is preferably flexible. Nipple connector 12 is formed of rubber or plastic. Valve 16 is generally formed of steel or plastic and has valve control 17, also made of steel or plastic. Hose 18 is generally formed of a flexible impermeable rubber with a supportive coating for handling. Variations of these parts are well known in the dental industry.

The sheath 14 is preferably formed of an impermeable lightweight material such that fluids do not penetrate it with ease and such that it is easy to handle. Specifically, sheath 14 can be formed of plastic. Alternatively, exterior surface 20 of sheath 14 can be absorbent and interior surface 22, towards the instrument, can be impermeable. For example, exterior surface 20 can be a layer formed of cotton fibers or a cotton sheet which is adhered to surface 22. Other suitable materials are well known in the dental industry, paper industry and diaper industry.

As shown in FIG. 1, the sheath 14 extends circumferentially from nipple 12 at juncture 26 to cover the dental instrument, valve 16 and hose 18. As described below in connection with FIG. 3, the sheath 14, nipple connector 12 and probe 11 can be manufactured as an integral unit. Alternatively, just the sheath 14 and probe 11 can be an integral unit and the nipple connector can be attached to the instrument after attachment of the sheath/probe.

Figure 2:
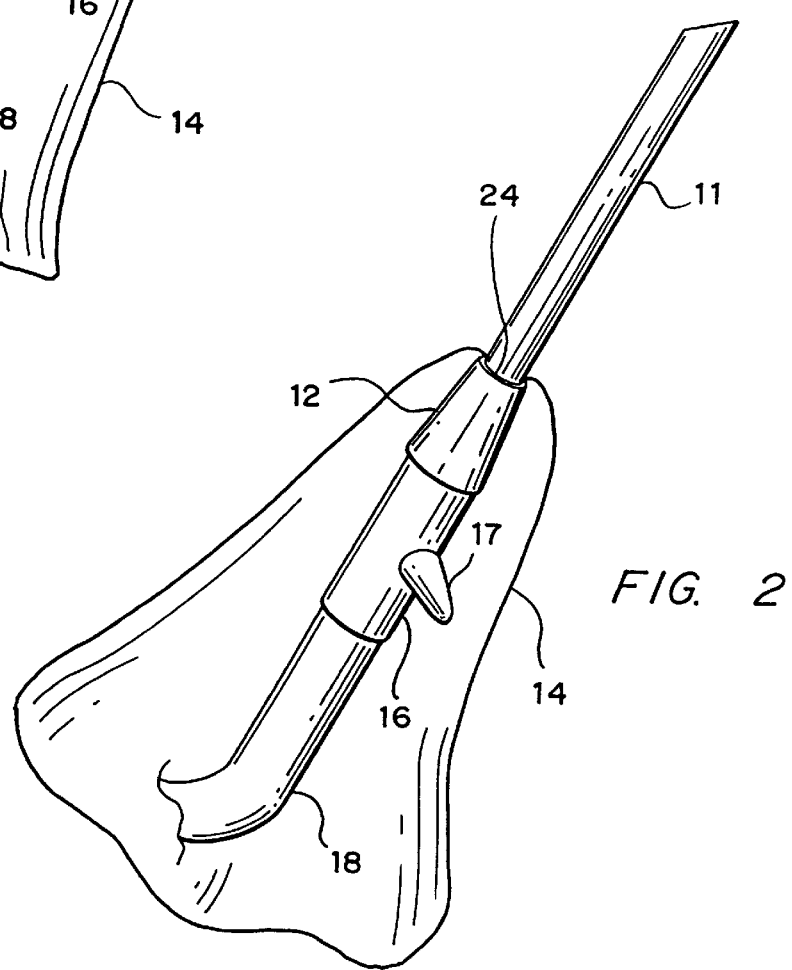
FIG. 2 illustrates a second embodiment of a barrier device installed on a saliva ejector instrument, wherein the connecting nipple is protected by the sheath.

FIG. 2 illustrates an embodiment that is similar to that illustrated by FIG. 1 except that sheath 14 extends from junction 24 between the nipple 12 and the ejector probe 11. Therefore, the embodiment shown in FIG. 2 protects the nipple 12, the valve 16, and hose 18.

FIG. 3 illustrates a preferred embodiment wherein probe 11, nipple 12, and sheath 14 are manufactured as a single disposable unit 27. To manufacture such a unit, probe 11 and nipple 12 can be molded as one unit or molded separately and then fitted or sealed together. Sheath 14 can be formed separately and then heat sealed, adhered, or otherwise fastened to either nipple 12 or probe 11. Alternatively, sheath 14 can be attached to probe 11 and then nipple connector 12 attached to probe 11 or sheath 14.

To use the device, the dental care provider wearing clean or fresh gloves connects the device to the valve 16 either by inserting the end of the probe 11 near the sheath into the valve and/or by attaching nipple 12 of the integral unit to the valve 16. Sheath 14 drapes down around the instrument to be protected. If nipple connector 12 is a separate piece it can be attached at this point. The instrument under the sheet 14 should not be touched with contaminated hands while assembling the device. The user places a hand over the sheath 14 to hold the instrument in the region of valve 16. The valve control 17 can therefore be adjusted without exposing the valve 16 and hose 18 to infectious agents on the user's glove. Moreover, the user does not place contaminating agents on the instrument surface. After use, the sheath, nipple connector, and probe are removed from the instrument and discarded.

FIG. 4 illustrates another preferred embodiment wherein ejector probe 11 and sheath 14 are formed as a single unit 29. Sheath 14 is connected to probe 11 at junction 28 by heat sealing or by use of adhesives. Alternatively, a fastener such as an O ring (not shown) can be used to retain sheath 14 on probe 11. In use, probe 11 is connected to valve 16 using adaptor 30, shown in FIG. 4, or by frictional insertion into valve 16, and sheath 14 is draped over the instrument to be protected. A nipple connector can be fitted over probe 11 to more tightly hold sheath 14 to probe 11.

FIG. 5 shows sheath 14 as manufactured independently. The dotted lines represent an instrument which is extended out from under sheath 14. Sheath 14 has orifice 31 having neck 32. Alternatively, neck 32 can be perforated such that orifice 30 is formed when the user penetrates the region within neck 32. Neck 32 can be formed to correspond to the size sufficient to protect the instrument which needs to be protected. Neck 32 can be provided with an elastic fastener or tape to help secure the neck 32 to the instrumentation. Sheath 14 can be draped over any dental instrument, accessory or body part.

FIG. 6 illustrates a preferred embodiment of the device for use with an air/water supply instrument 33. Probe, or syringe tip, 34 extends from nipple 40 at juncture 42. Nipple 40 is formed of plastic or rubber and connects to the air/water supply instrument 36. The device can be supplied as an integral unit including tip 34, sheath 14 and nipple 40. Alternatively the device can include only sheath 14 and tip 34, as shown in FIG. 7.

As illustrated in FIG. 7, sheath 14 is attached to tip 34 at junction 32. Sheath 14 can be formed independently as shown in FIG. 5 and then tightly attached to the probe at juncture 32 using an O ring (not shown), for example. The device and instrument are used as described above for the suction instrument. A user wearing fresh gloves can use and hold instrument 33 without contaminating the instrument or contaminating anything else touched after using the instrument. After use, the entire unit is discarded.

Modifications and variations of the devices and methods described herein will be obvious to those skilled in the art from the foregoing description, and are intended to come within the scope of the appended claims.

I claim:

1. A disposable barrier device for use with a dental instrument to prevent saliva from contacting the instrument and to prevent transfer of contaminants, comprising:

a probe that can be attached to the instrument for insertion into a dental patient's mouth to perform a function;

an elongated sheath that is substantially impervious to contaminants having one end circumferentially attached to the probe; and a flexible nipple connector on the exterior of the sheath that connects the probe to the instrument;

wherein when the probe is connected to the instrument the sheath covers the portion of the instrument that is contacted during use of the instrument.

2. The barrier device of claim 1 wherein the probe and the sheath are manufactured as an integral unit.

3. The barrier device of claim 1 wherein the nipple is integrally formed with the probe and the sheath.

4. The barrier device of claim 1 wherein the dental instrument is a saliva ejector instrument.

5. The barrier device of claim 1 wherein the dental instrument is an air/water supply instrument.

6. The barrier device of claim 1 wherein the sheath is made from a multilayer fabric, having an absorbent layer and a fluid impervious layer.

* * * * *